US006254828B1

(12) United States Patent
LaCount

(10) Patent No.: US 6,254,828 B1
(45) Date of Patent: Jul. 3, 2001

(54) FLUID CELL SUBSTANCE ANALYSIS AND CALIBRATION METHODS

(76) Inventor: Robert B. LaCount, 403 Arbor Ct., Waynesburg, PA (US) 15370

( * ) Notice: Subject to any disclaimer, the term of this patent is extended or adjusted under 35 U.S.C. 154(b) by 0 days.

(21) Appl. No.: 08/047,512

(22) Filed: Apr. 19, 1993

Related U.S. Application Data

(63) Continuation-in-part of application No. 07/692,981, filed on Apr. 29, 1991, now Pat. No. 5,204,270, and a continuation-in-part of application No. 07/849,501, filed on Mar. 11, 1992, now Pat. No. 5,285,071.

(51) Int. Cl.[7] ............................ G01N 31/12; G01N 21/05
(52) U.S. Cl. ............................ 422/78; 250/343; 250/373; 256/246; 422/80; 422/82.05; 422/91; 436/157; 436/181
(58) Field of Search ........................... 250/343–345, 250/373; 356/51, 246, 410, 436–440; 422/78, 80, 82.05, 82.09, 91; 436/155, 157, 181

(56) References Cited

U.S. PATENT DOCUMENTS

| 3,079,505 | * | 2/1963 | Weir et al. .......................... 356/51 |
| 3,236,602 | * | 2/1966 | Isreeli ................................ 356/246 |
| 3,279,308 | * | 10/1966 | Bartz et al. ..................... 250/343 X |
| 3,319,512 | * | 5/1967 | Isreeli ................................ 422/65 X |
| 3,428,433 | | 2/1969 | Ehrenberger et al. .............. 422/78 |
| 3,435,209 | * | 3/1969 | Keahl ............................. 250/373 X |
| 3,512,398 | * | 5/1970 | Hrdina ............................ 356/246 |
| 3,524,709 | * | 8/1970 | Hrding ............................ 356/246 |
| 3,614,243 | * | 10/1971 | Harvey ........................... 356/246 |
| 3,751,173 | * | 8/1973 | Sanz et al. ....................... 356/246 |

(List continued on next page.)

FOREIGN PATENT DOCUMENTS 2507541  5/1976  (DE) .
2407473  5/1979  (FR) .

OTHER PUBLICATIONS

J.E. Stewart *Appl. Optics* 1979, 18, 5–6.*
N.R. Trenner et al. *Chem. Abstr.* 1954, 48 , 2516f.*
D.S. Russell Can. J. Chem, 1958, 36, 1745–1746.*
N.L. Alpert et al. "IR Theory and Practice of Infrared Spectroscopy", Plenum Press: New York, 1970, pp. 66–68.*
L. Swope *Rev. Sci: Instrum.* 1971, 42, 1502–1504.*

(List continued on next page.)

*Primary Examiner*—Arlen Soderquist
(74) *Attorney, Agent, or Firm*—James Creighton Wray; Meera P. Narasimhan

(57) ABSTRACT

Gases flow to individual gas analysis cells. The cells are sequentially aligned with an infrared detector, which senses the composition and quantities of the gas components. Each elongated cell is tapered inward toward the center from cell windows at the ends. Volume is reduced from a conventional cell, while permitting maximum interaction of gas with the light beam. Reduced volume and angulation of the cell inlets provide rapid purgings of the cell, providing shorter cycles between detections. For coal and other high molecular weight samples, from 50% to 100% oxygen is introduced to the tubes. Cells are suspended from adjustable holders on a frame which is spaced from a table. The table is moved by a linear motor and a fixed platen. Sides of the table are shielded to prevent electromagnetic and magnetic motor interference with detected results. The entire table, cells, mounting plate and linear motor are mounted in a housing with aligned holes for the analysis energy source and detector. The gas cells are calibrated for carbon dioxide and water vapor with a mass flow controlled oxidized fuel gas from a single analyzed source of such gas, oxygen and inert gas. Other calibration gases may be included, generated or added in the calibration gas stream.

18 Claims, 8 Drawing Sheets

U.S. PATENT DOCUMENTS

| | | | | |
|---|---|---|---|---|
| 3,761,187 | * | 9/1973 | Dittrich et al. | 356/246 |
| 3,784,359 | | 1/1974 | Parth | 422/79 |
| 3,838,972 | | 10/1974 | Richards et al. | 436/100 |
| 3,865,495 | * | 2/1975 | Sanz et al. | 356/246 |
| 3,950,101 | * | 4/1976 | Dewey, Jr. | 250/345 X |
| 3,985,505 | | 10/1976 | Bredeweg et al. | 436/160 |
| 4,083,367 | * | 4/1978 | Portner et al. | 356/51 X |
| 4,181,437 | * | 1/1980 | Rossiter | 356/246 |
| 4,192,614 | * | 3/1980 | de Mey, II et al. | 356/410 |
| 4,238,198 | | 12/1980 | Swaim et al. | 436/120 |
| 4,591,268 | * | 5/1986 | Lew | 356/246 X |
| 4,736,103 | * | 4/1988 | Nelson et al. | 250/343 |
| 4,787,750 | * | 11/1988 | Nelson et al. | 356/437 |
| 4,822,166 | * | 4/1989 | Rossiter | 356/246 |
| 4,823,168 | * | 4/1989 | Kamahori et al. | 356/246 |
| 4,824,790 | | 4/1989 | Carangelo et al. | 422/80 |
| 4,844,611 | * | 7/1989 | Imahashi et al. | 356/246 |
| 4,845,040 | | 7/1989 | Moon et al. | 422/78 |
| 4,886,356 | * | 12/1989 | Paradis | 356/246 |
| 4,889,992 | * | 12/1989 | Hoberman | 250/343 |
| 5,146,283 | * | 9/1992 | Parnoff et al. | 356/440 X |
| 5,204,270 | * | 4/1993 | LaCount | 436/157 |
| 5,285,071 | * | 2/1994 | LaCount | 250/343 |

OTHER PUBLICATIONS

LaCount et al., "Coal Characterized by Programmed–Temperature Oxidation", Electric Power Research Institute, 1–13 (U.S.A. 1991).

LaCount et al., "Contruction and Operation of a Controlled–Atmosphere . . . ", Pittsburgh Energy Technology Center, 2–22 (U.S.A. 1983).

LaCount et al., "Thermal Oxidative Degradation of Coal . . . ", New Approaches in Coal Chemistry, 415–426 (U.S.A. 1981).

Stock et al., "Sulfur Distribution in American Bituminous Coals", Energy and Fuels, 3:651–661 (U.S.A. 1989).

Friedman, "Sulfur Analysis of Coal—A Critical Evaluation", Electric Power Research Institute, 3–12 (U.S.A. 1990).

LaCount et al., "Sulfur in Coal by Programmed–Temperature Oxidation", Fuel; The Science and Technology of Fuel and Energy, 66:909–913 (U.S.A. 1987).

IR/FTIR Accessories and Supplies Catalog, Buick Scientific, 15 (U.S.A. 1990).

Infrared Accessories and Supplies, Spectra Tech, 32–33 (U.S.A. 1990).

IR/FTIR, Spectra Tech, 6–7 (U.S.A. 1990). Barnes Analytical.

Perkin Elmer—Infrared Spectroscopy Supplies Catalog, PE Express, 26–27 (U.S.A. 1989).

Calkins, "Investigation of Organic Sulfur—Containing Structures in Coal by Flash Pyrolysis Experiments", Energy and Fuels, 1:59–64 (U.S.A. 1987).

Boudou, "Identification of Some Sulphur Species in a High Organic Sulphur Coal", Fuel, 66:1558–1568 (France, 1987).

Boudou et al., "Continuous Gas Detection During Heating of Coal and Kerogen", New Methodologies for Coal Characterization, 1–5 (France, undated).

Boudou, "Determination of the Nature of Organic Sulphur in a High Organic Sulphur Coal", Internal Conference on Coal Science, 13–14 (France, 1987).

Fixari et al., "Oxidative Pyroanalysis: Elemental Analysis in Volatile and Nonvolatile Fractions of Coals . . . ", Fuel, 69:851–855 (France, 1990).

Solomon et al.. "Analysis of the Argonne Premium Coal Samples . . . ", Energy and Fuels, 4:319–333 (U.S.A. 1990).

Carangelo et al., "Application of TG–FT–i.r. to Study Hydrocabon Structure and Kinetics", Fuel, 66:960–967 (U.S.A. 1987).

Carangelo et al., "Quantitative Evolved Gas Analysis From an Indianhead Zap Lignite", Advanced Fuel Research, 1–3 (U.S.A., undated).

Whelan, "Thermogravimetric Fourier Transform Infrared Spectroscopy . . . ", Energy and Fuels, 2:65–73 (U.S.A. 1987).

* cited by examiner

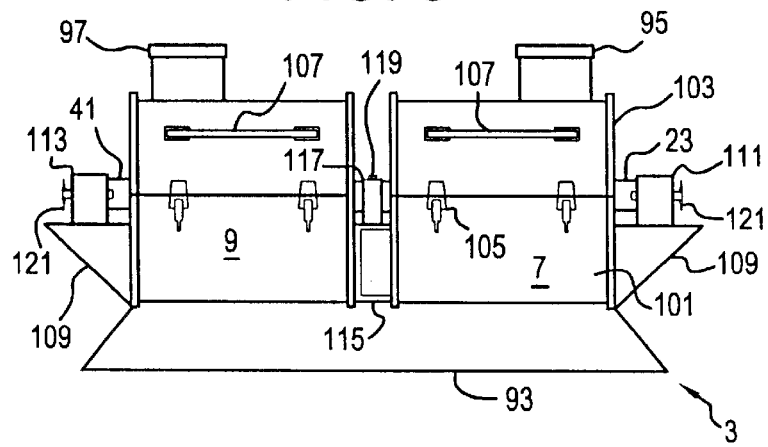
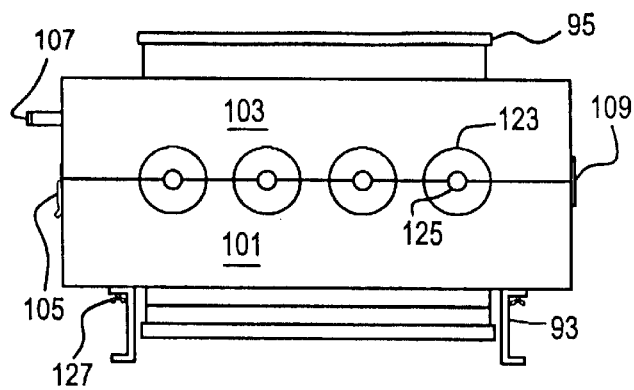
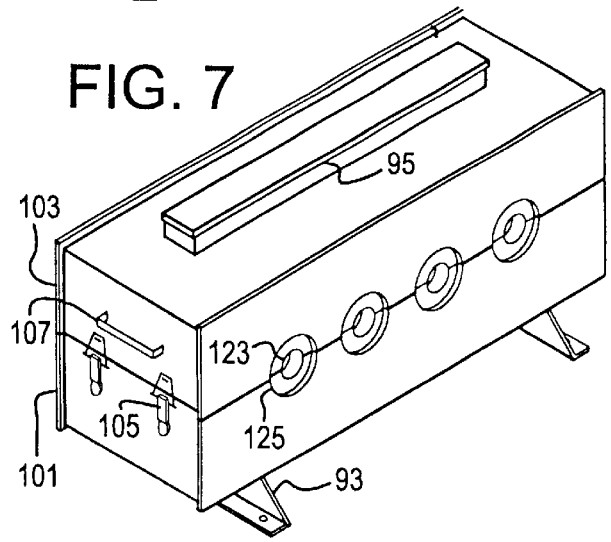
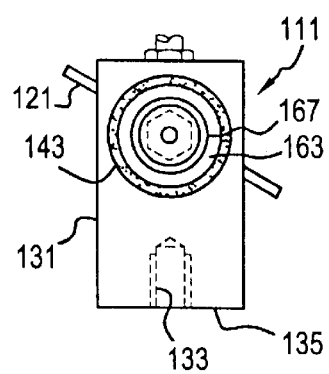

FLUID CELL SUBSTANCE ANALYSIS AND CALIBRATION METHODS

This is is a continuation-in-part of application Ser. No. 07/692,981 filed Apr. 29, 1991, which will have issued Apr. 20, 1993 as U.S. Pat. No. 5,204,270, and application Ser. No. 07/849,501 filed Mar. 11, 1992, now U.S. Pat. No. 5,285,071, which are incorporated herein by reference.

BACKGROUND OF THE INVENTION

This invention concerns gas analysis apparatus and methods.

A need continues to exist for apparatus for a systematic analysis of gases.

Existing gas analysis cells have large volumes. Consequently a large volume of gas must be flowed into and out of a cell before a new significant reading may be taken. Quantities of available gases make purging inconvenient, wasteful and time consuming.

A need exists for analysis cells which may be readily filled, read and purged.

Instrument calibration requires several steps. A need exists for rapid, accurate calibration.

Gas analysis cells may be large and heavy and many cells may be required. A need exists for a system that is capable of performing such analysis.

SUMMARY OF THE INVENTION

The present invention provides solutions to the long standing needs.

In the present invention, a furnace with two hot zones holds multiple analysis tubes. Each tube has a separable sample-packing section positioned in the first hot zone and a catalyst-packing section positioned in the second hot zone. A mass flow controller is connected to an inlet of each sample packing tube, and gas is supplied to the mass flow controller. Oxygen is supplied through a mass flow controller to each tube to either or both of an inlet of the first tube and an intermediate portion between the tube sections to intermingle with and oxidize the entrained gases evolved from the sample. Oxidation of those gases is completed in the catalyst in each second tube section. A thermocouple within the catalyst pack controls the temperature of the second hot zone, which remains substantially fixed. A thermocouple within at least one of the sample packings controls the uniform increase of temperature in the first hot zone, reducing the added heat immediately when an exothermic condition is sensed within the sample. Oxidized gases flow from outlets of the tubes to individual gas cells, and the gas flows through and out of the cells. The cells are sequentially periodically aligned with an infrared detector, which senses the composition and quantities of the gas components. Each elongated cell is tapered inward toward the center from cell windows at the end. Each cell contains a volume reduced from a conventional cell, while permitting maximum interaction of gas with the light beam. Reduced volume and angulation of the cell inlets provide rapid purgings of the cell, providing shorter cycles between detections. For coal and other high molecular weight samples, oxygen makes up from 50% to 100% of the gas introduced into the tubes.

This invention provides instruments and analysis equipment for a multi-sample by controlled-atmosphere programmed-temperature oxidation.

Before conception of the invention, a problem existed in determining whether sulfur was present in organic or inorganic compounds, for example in inorganic pyrite, which is iron disulfide. Exothermic reactions obscured results. The inventor experimented with gradually changing the oxygen concentration from 10% in argon to 16% in argon. A slight shift of the pyritic sulfur toward evolution at a higher temperature was noticed under those conditions. Continued increasing of the concentration to 20% and finally to 100% oxygen surprisingly improved results. The 100% oxygen experiment indicated that the pyritic sulfur evolution was moved to higher temperature and was evolved after the higher temperature organic sulfur peak, permitting both peaks to be resolved.

Further work showed that celite or other silica products such as silicic acid, silica gel, and synthetic silicas when used as diluents for the coal resulted in a more highly resolved pyrite evolution peak compared to tungsten trioxide, a previous diluent.

This invention provides use of the higher oxygen concentration ranges (50%–100%) and the use of tungsten trioxide, zirconium dioxide, silicon dioxide products, preferably celite, and other metal oxides as diluents. The invention also provides the use of metal oxides or other catalysts to oxidize organic compounds to oxides of carbon, hydrogen, sulfur and nitrogen. The metal oxides or other catalysts must not interact, absorb and re-emit, the oxide gases produced in the oxidation reaction.

The technique of the invention can be used to characterize coals, oilshales, carbon deposits on refinery and other catalysts, polymers, and other high molecular weight materials. In addition to the sulfur dioxide evolution profiles, the carbon dioxide, water, and nitrogen dioxide profiles are obtained. This allows characterization of the carbon, sulfur, hydrogen, and nitrogen in the material tested and analysis for those elements in the material.

The present invention is suited to resolve the gases evolved from the pyritic and the more oxidatively resistant organic sulfur in the material oxidized. The best conditions are produced in 100% oxygen with a silica product such as celite as a diluent for the material being oxidized. Preferably particle size of solids being oxidized and diluent are about −60 mesh or smaller. Preferably the diluent and the sample substance are well mixed and are uniformly distributed. However, high oxygen concentrations such as 50%–100% oxygen and other diluents such as silicic acid, silica gel, synthetic silicas, tungsten trioxide, zirconium dioxide, and other metal oxides may be used.

The technique is applicable to characterizing many substances, such as for example coals, treated coals, oil shales, polymers, carbon deposits on refinery and other catalysts, and other high molecular weight substances. The diluent or a screen may follow the sample. Preferably finely divided quartz wool previously heat treated at about 1100° C. is positioned upstream and downstream of the simple to hold the sample in position. Preferably quartz rods held in place by quartz wool are inserted in any void in the sample and catalyst tubes to reduce internal volume and promote flow-through of the evolved gases.

The invention evolves a material from the sample and oxidizes the evolved material.

When run in the oxidation mode, most of the oxidation occurs in the sample. The second tube and the catalyst complete the oxidation and establish $SO_2$—$SO_3$ equilibrium.

Characterizing the substances under the oxidizing conditions described above is one of the objects of the invention. The evolved gas concentration versus time and/or temperature profiles for carbon dioxide, sulfur dioxide, nitrogen dioxide, and water are unique. Additionally, analyses for the amount of carbon, sulfur, nitrogen, and hydrogen in the sample oxidized are obtained by calculations based on the evolved gases.

The instrument can also be used in a pyrolysis mode where an inert gas is passed through the sample and diluent (silica product and/or metal oxides) with gradually increasing temperature. Gases are evolved from the sample and are oxidized by oxygen supplied to the gas stream as it enters the second hot zone. The gases produced, carbon dioxide, sulfur dioxide, nitrogen dioxide, and writer provide, after analysis, concentration versus time and/or temperature profiles for the pyrolysis gases produced from the substance being tested. Integrating the evolved gas profiles and relating them to the amount of carbon, hydrogen, sulfur, and nitrogen produced by pyrolysis with time data provides information similar to that of a thermal gravimetric analysis (TGA) experiment, in which samples are weighed as gases evolve. In addition, this provides information on the nature of the elemental composition of the volatile pyrolysis products.

A new multi-tube horizontal split combustion furnace made with two to six or more tubes has been designed and is incorporated into the system. A prototype version contains four combustion tubes and the temperature may be increased or ramped over a wide range of temperatures. However, 2° C. to 10° C., and preferably 3° C. per minute are the preferred rates of increase. The furnace, mass flow controllers for the inlet gases, pressure transducers and regulation system, stepper motor for cell movement, and a number of relays and the whole system may be controlled from one or more micro computers.

The furnace includes a second hot zone with oxidizing tubes, after each of the combustion tubes, containing tungsten trioxide, zirconium dioxide, a metal, or other metal oxide catalysts, heated to approximately 1050° C. The catalysts oxidize any gases that are not already in their highest oxidation state. Additionally, the second hot zone maximizes the sulfur dioxide concentration relative to sulfur trioxide. The second hot zone also assures a constant temperature for the emerging gas. The catalyst preferably does not interact, absorb or re-emit the evolved gases at different temperatures. The catalyst may absorb or emit the evolved gases at the same temperature.

Each combustion train in the new multi-tube furnace is fitted with an oxygen inlet between the two hot zones. That permits the system to be used in a pyrolysis mode, with an inert gas flowing through the system. The pyrolysis gases are all converted to oxides (carbon dioxide, nitrogen dioxide, sulfur dioxide, and water) in the second hot zone. Quantitative pyrolysis experiments, as well as oxidation experiments, can be conducted in any one or all of the combustion trains. The analyses can be completed by analyzing products of the organic compounds and other gases after they pass through the second hot zone using tungsten trioxide, zirconium dioxide, or other metal or metal oxide as an oxidation catalyst. The use of the second hot zone to oxidize the pyrolysis gases simplifies quantitative analysis of the gaseous pyrolysis mixture.

The split tube design allows removal and repacking of the sample tubes. The second hot zone tube is for catalytic conversion and catalyst tubes do not have to be repacked each time a new sample is analyzed.

The thermocouples that control the furnace are located in the combustion tubes and are embedded in the samples during the experiment. Employing a measuring thermocouple embedded in the samples ensures accurate sample temperature and controls furnace temperature. This thermocouple, used as the control thermocouple, provides a more even temperature ramp. The thermocouple can sense an exotherm and call for reduced heating sooner than a thermocouple mounted externally on the combustion tube.

The gases pass through a newly designed gas flow cell for analysis by a fourier transform infrared (FTIR) spectrometer. The gas cell is designed to take full advantage of the elliptical, almost cone-shaped, infrared light beam produced by FTIR spectrometers. The cell contains approximately one-third less gas volume than a conventional cell, and at the same time produces an infrared spectrum of the same intensity as a conventional infrared gas analysis cell of the same length and diameter.

Since the cell contains one-third less volume than a conventional gas cell, the clearing time is about one-third shorter. The cell tapers inward from the ends to the middle. This design shows some interesting flow patterns which might cause the clearing time of the cell to vary as a function of the angle of a directed flow inlet gas stream. At certain inlet angles the cell clearing time is significantly less relative to a non-directed inlet flow. These same inlet angle experiments were also carried out on a non-tapered gas cell that was identical to the above cell, except for the taper and cell volume. The cell clearing time was again found to be a function of the angle of the inlet gas stream. Thus, the directed flow modification is an important feature that also can be incorporated into conventional gas cells.

The properties of smaller volume and shorter clearing time due to the smaller volume and the directed flow make the tapered cell desirable for a wide variety of infrared gas cell applications.

The cell body can be fabricated from glass, steel, or a variety of polymeric materials in any length that will fit in a FTIR cell compartment. Any type of infrared window material (NaCl, $CaF_2$, KBr, $BaF_2$, CsI, CsBr, KRS-5, ZnSe, AgCl, Intran-2 or fused silica) may be attached through any conventional state-of-the-art techniques, such as a screw cap with seals threaded onto glass, metal, or plastics or to plastic threaded material snapped around the cell; metal or plastic rims (one behind a flange on the cell) screwed together with the window and seals between the rims.

The cell inlet and outlet can be fitted with simple tubulations at angles from 0° to 360° relative a long axis of the cell for flow through applications. Tubulation on an inside of a cell inlet can be directed at the best angle to give minimum clearing time. Septa for injection of gases directly into the cell, stopcock closures, or different fittings attach a variety of plastic or metal tubing to the cell.

The cell can be heated by a simple heat tape, by a controlled, enclosed heater mounted as an integral part of the cell, or by a number of other state-of-the-art heating methods.

The cell can be fabricated for use at medium or high pressures.

"Beam conforming cells" have been designed for older infrared instruments in which the beam emerged from the instrument in a rectangular shape. However, those differ significantly from the functional shape of the present cell.

A multi-cell holder has been designed to position one of four gas cells in the spectrometer beam for analysis normally every 15 seconds. A longer or shorter analysis timing sequence may be used. A stepper motor with a worm drive train moves the cell holder plate on command from a timer or a computer command. The movable cell holder may be adapted to any infrared instrument currently manufactured.

A mass flow controlled gas mixture is introduced to the combustion tubes. The pressure in the system is measured with a pressure transducer. A pressure regulation system on this instrument is used to keep the pressure in each gas cell constant.

The information obtained from the new instrumental system includes pyrolysis data on the amount of carbon, hydrogen, sulfur and nitrogen lost as the temperature of the sample is increased. That information is useful from the single or multi-tube furnace system. The evolved gas information is integrated to provide information similar to that obtained from thermal gravimetric analysis. In thermal gravimetric analysis (TGA) the sample is placed on a sensitive balance and is heated. The weight loss is measured as a function of temperature. In the present pyrolysis technique, the evolved gases are quantitatively measured and integrated over time to provide information on the amount of sample lost with time. The profiles resemble those produced in a TGA experiment, except that instead of mass the elemental composition of the carbon, hydrogen, nitrogen and sulfur lost by oxidation or pyrolysis is obtained.

A description of the present pyrolysis technique is a controlled-atmosphere programmed-temperature oxidation evolved gas analysis (CAPTO-EGA).

A preferred furnace has first and second hot zones. Multiple tubes extend between the first zone and the second zone. A catalyst is positioned in the tubes in the second zone. Sample-diluent mixtures are packed in parts of the tubes in the first zone. Gas flows into the inlets of the tubes in the first zone and flows through the samples, entraining pyrolysis gases from the samples. An oxygen source connected to the gas introduction means flows oxygen into the tubes for oxidizing the pyrolysis gases before and as the gases flow through the catalyst in the second hot zone. Outlets of the tubes are connected to gas analyzer cells for supplying oxidized pyrolysis gas to the cells, and exhaust lines connected to the cells for flowing gas out from the analysis cells.

A preferred gas supply is an oxygen source. A mass flow controller is connected to the oxygen source. A pressure transducer is connected between the mass flow controller and the tube for measuring pressure as the mass flow controller supplies oxygen to the inlet of a tube.

Plural mass flow controllers and plural transducers are each connected in parallel between an oxygen tank and distinct tubes.

Another embodiment has a source of inert gas and inert gas mass flow controllers connected to the inlets of the combustion tubes for supplying inert gas alone or in combination with oxygen to the combustion tubes.

Plural inert gas mass flow controllers are each connected in parallel between the source of inert gas and the inlets of the tubes.

Preferably the tubes are horizontal tubes, and the furnace is divided by a vertical wall into two heated zones.

In a preferred embodiment, an oxygen relay is connected to each mass flow controller and to an intermediate portion of a tube for supplying oxygen to an intermediate portion of the tube and to pyrolysis gases from the sample before the gases pass into the catalyst.

Preferably one relay is connected to each mass flow controller for receiving oxygen therefrom. A first oxygen supply line is connected between each relay and each pressure transducer connected to the inlet of each tube. A second supply line is connected between each relay and an intermediate portion of each tube for supplying oxygen to each tube between the sample and the catalyst.

Sample thermocouples extend through inlets of each tube into the sample packed in the tube for controlling furnace temperature in the first hot zone.

Catalyst thermocouples are inserted through outlets of the tubes into catalysts within the tubes for controlling temperature in the second hot zone of the furnace.

Plural cells are each connected to a tube extending from an outlet of the combustion tube.

In a preferred form of the invention, the gas analyzer cells are aligned parallel and are mounted on a table. A motor moves the table transversely. An infrared light beam source projects an infrared light beam through the cells. A detector aligned with the source on an opposite side of the table receives light projected through the cells. The motor moves each cell into alignment and out of alignment with the infrared light beam in a predetermined sequential relationship.

Each cell has a tapered body which is relatively wide at the top, relatively narrow in the middle, and relatively wide at the bottom. A cell window forms the top of the cell, and a second cell window forms a bottom of the cell. A cell inlet is connected to a wall of the cell near the upper cell window, and a cell outlet is connected to a wall of the cell near the lower cell window. The inlet and outlet are directly across from one another or any angle to each other.

The tapered cell body is preferably a truncated, generally conical upper cell wall and a truncated, generally conical lower cell wall joined medially in a small waist portion.

The preferred gas inlet is a tube which extends through the upper cell wall at an angle of from about 0° to about 30° from the cell window. Preferably the inlet has an open end which points upwardly or toward the near end of the cell at about 0° to 60° to a vertical direction. An angle of up to about 90° is useful; about 0° to 30° is preferred.

The inlet tube is aligned with the cell wall between a tangential and a radial position for swirling and purging gas from within the cell.

Gas is flowed angularly into a top of a cell and downward through a converging upper portion of the cell, and subsequently downward through a diverging lower portion of the cell and out through the cell outlet at the bottom of the cell.

In a preferred embodiment, the combustion tubes have removable first combustion sections which separate from the second catalyst sections. The combustion sections may be withdrawn and repacked with sample material.

The preferred method of quantitatively analyzing multiple samples includes parking samples in first tube sections and packing a catalyst in second tube sections. The first and second tube sections are placed in horizontal communicating alignment in a furnace having a first hot zone which receives the first tube sections, and a second hot zone which receives the second tube sections. The first hot zone is heated with a gradually increasing temperature, and heating the second hot zone is held at a constant elevated temperature. Gas is introduced into an inlet of each tube. Preferably the gas contains at least 50% oxygen. Heated resultant pyrolysis gases from the sample are entrained within the first tube section, while partially oxidizing the entrained gases. Oxygen may be supplied to the tubes between the sample and catalyst and mixing oxygen with the entrained pyrolysis gases, the gases are heated and oxidized in the heated catalyst within the second tube sections, completing oxidation of the gases. Gases flow out of outlets of the second tube sections and into inlets in plural gas cells connected separately to the outlets of the second catalyst-holding tube sections. Gas flows through the gas cells and is released gas from the gas cells under pressure regulation. The cells are selectively moved into alignment with an infrared beam, and influence on the infrared beam by gas within the cells is sensed with an electronic detector. Other detectors may be used, for example a Raman spectrograph. Non dispersive infrared detectors, mass spectrometry or gas chromatography may be used in lieu of the gas cell analysis fc)r the detection of products. Temperature within the first hot zone is raised at a slow rate of increase, and sequentially positioning the cells within the infrared light beam and detector during the increase in temperature in the first hot zone determines oxidized pyrolysis gases released from the samples and entrained and oxidized, and thereby determines content of the sample.

Preferably the increasing temperature in the first hot zone comprises increasing temperature at a rate of about 2° C. to 10° C. or about 3° C. per minute, while supplying an inert gas with the oxygen to an inlet of each first tube. The rate is chosen so that the products are released at different times and so that exothermic reactions are controlled or avoided.

Cells are preferably suspended from adjustable elements on a frame connected to a table which is moved by a self-contained shielded linear motor.

Calibration is provided by releasing an analyzed mixture of a hydrocarbon fuel gas, oxygen and an inert gas, completely oxidizing the mixture in a heated catalyst and using mass flow controlled resultant gases.

This invention provides a cell movement device for multiple stream analysis. A copending application contains a description of the device and its FTIR spectrometer application to evolved gas analysis (EGA) of multiple combustion streams using a slide powered by a motor. The copending patent application describes a general use of the cell positioner for gases and liquids and provides a linear motor as the drive mechanisms, in addition to a screw drive mechanism. The copending application also related to devices to align the cells and to a rotary positioning device.

Screw driven tables support and move any cells that one would wish to mount. However, the more compact cell positioner based on the use of linear motors has a 5 to 10 pound total weight limit for the cells that it will transport. This weight limit is adequate for the gas analysis cells used in the present device. However, the cell positioner device with the linear motor may have difficulty in moving heavy, longer pathlength and multiple path cells that may be required to analyze components in low concentrations. Some examples of the components present in experiments carried out using a smaller sample size or some of the components present in stack gas or air analysis may require the movement of a 20 to 25 pound load. To provide a cell positioner of more general use, the positioner has been modified by placing support rods (ball way modules/ball splines or other support rods, or rods with linear bearings) on both sides of the linear motor. These tracks or rods support the mounting plate and cells weight, and the linear motor simply acts as a locomotive to push the payload along the tracks or rods. In this manner higher weight cells can be accommodated using a compact linear motor.

In addition, the invention provides a method and software that allows the completion of a reference spectrum before, during or after each pass of the cell positioner through the cells. Previously a reference spectra was completed near the beginning of a run before reaction had taken place, and near the end of a run after reaction had taken place, to determine a baseline. If the system baseline should drift significantly plus or minus over the five to six hours of the run, this could introduce some error into the results. This has not been a serious problem, as evidenced by good quantitative results on known systems. However, to provide a more flexible system, a method has been developed where one can select that the baseline be determined as described above (at the beginning and end of a five to six hour run) or that a reference spectrum be completed for each cell measured (approximately every 15 seconds with the present four cells) or sometime during each pass of the cells through the spectrometer (approximately every minute with four cells present) for use in determining a baseline.

The invention provides for more rapid purging and filing by using tapered cells and water calibration methods.

The invention provides the method of using multiple cells mounted on a motorized slide for the purpose of analyzing multiple fluid streams (flowing or non-flowing gas, liquid or solids) and reference by using one Fourier Transform Infrared (FTIR) spectrometer or other infrared type of spectrometer.

The invention provides the method of interrogating each sample or reference stream for analysis by repeatedly moving each cell into alignment with the infrared beam on a periodic basis for the purpose of qualitatively and quantitatively analyzing the components (monitoring the components and the change in concentration of the components) in the stream with respect to time.

Also provided by the invention is the method of mounting the analysis cells and cell positioner motor and system housing for use in an existing cell compartment of a commercial infrared spectrometer.

The invention provides the method of using one of the other infrared sampling port/detector combinations provided on commercial FTIR's or other infrared spectrometers and mounting the analysis cells and cell positioner motor and system housing for use at the port/detector combination.

The invention provides the method of mounting multiple commercial infrared cells of the varied or variable pathlengths for gases, liquids or solids on the cell positioner table for the purpose of analysis as described above.

Another object of the invention if the provision of the method of using the cells and cell positioning system to obtain infrared spectral analysis measurements before and after the experiment for the purpose of determining a baseline for the experiment.

The invention has as an object the provision of the method of using reference cells and sample cells and a cell positioning system to determine a baseline each time a sample cell is positioned and analyzed.

The invention provides the method of using reference cells and sample cells and cell positioning system to determine a baseline before, during or after the cell positioner has moved through one (or any designated number) complete analysis cycle of the cells.

An object of the invention is to provide a cell positioner table for the mounting of commercial liquid or long pathlength gas cells.

Another object of the invention is the provision of support rods with linear bearings, ball way modules/ball splines or other support rods mounted on either side of and in alignment with a linear motor to support the weight of the positioning table and of any analysis cells, including multiple pass gas cells, mounted on the positioning table.

The above outlines procedures and hardware are important for the more general use of the positioning table. A screw drive or a belt drive may replace the linear motor or the supported linear motor. The drawing shows the current linear motor and support rods. A steel housing for the positioning motor and platen provides shielding.

These and further and other objects and features of the invention are apparent in the disclosure, which includes the above and ongoing written specification, with the claims and the drawings.

BRIEF DESCRIPTION OF THE DRAWINGS

FIG. 5 is a front elevation of the furnace shown in Figure 4.

FIG. 6 is a side elevation of the furnace shown in FIGS. 4 and 5.

FIG. 7 is a perspective view of one furnace section.

FIG. 8 is an end elevation of an end fitting used to hold tube sections in the furnace.

DETAILED DESCRIPTION OF THE DRAWINGS

Figure 1:
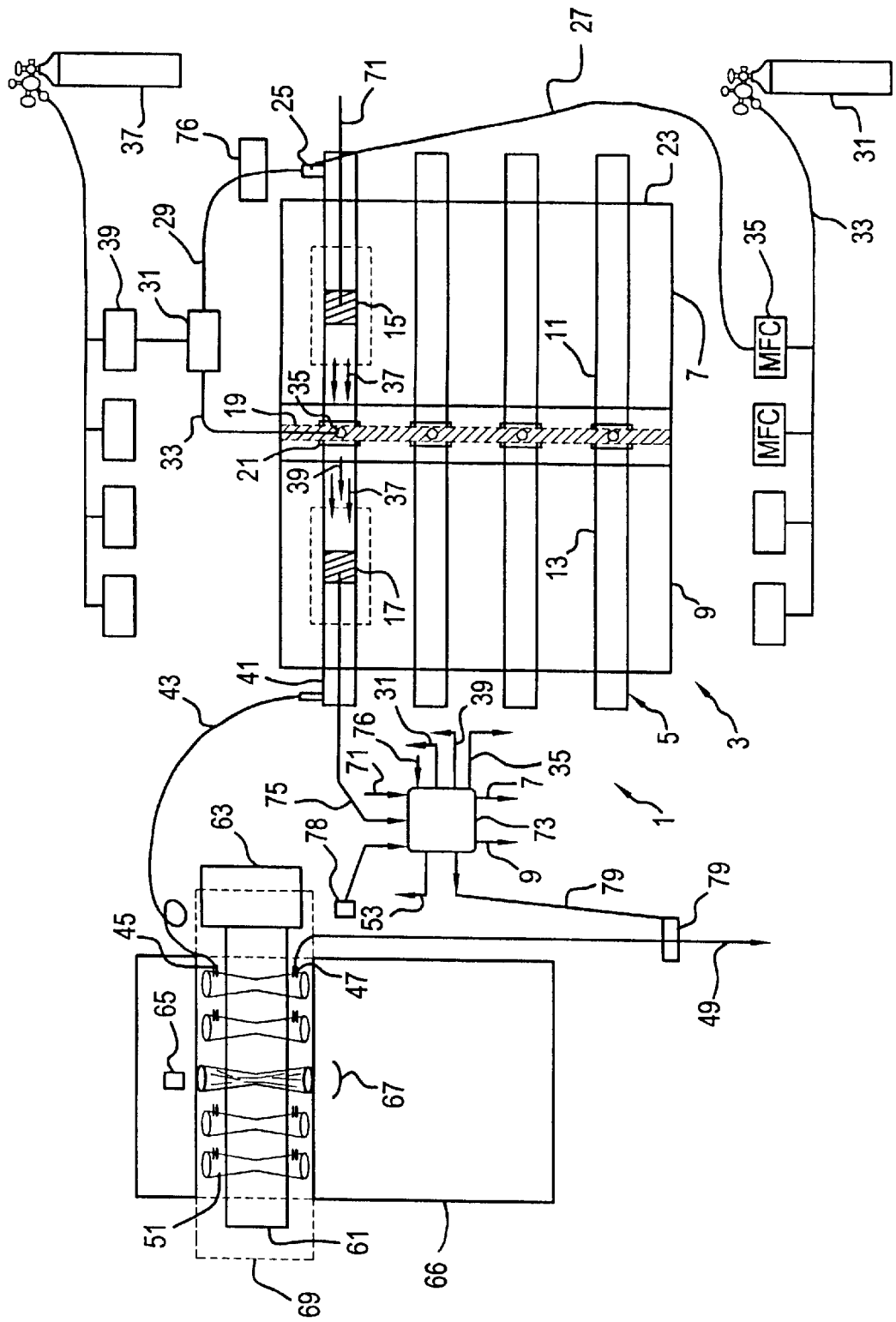
FIG. 1 is an overall system schematic drawing.

Referring to FIG. 1, a sample analysis system of the present invention is generally referred to by the numeral 1. The system has a furnace 3, which holds horizontal tubes 5, in this case four. The furnace is divided into two hot zones 7 and 9. Tubes 5 are divided into sections 11 and 13. First sections 11 hold a sample 15. Second sections 13 hold a catalyst 17. The hot zones are divided by an insulated wall 19, which includes plural tube connectors 21, as will later be described. Each tube section 11 has an inlet 23, on which is provided a gas supply connector 25. Gas is supplied through separate supply tubes 27 and/or oxygen is supplied through supply tubes 29 to separate inlets 23 of the tubes.

When an inert gas is used, an inert gas such as argon from a source 31 is supplied on line 33, which is connected to individual mass flow controllers 35, each of which is connected to a line 27, and each line 27 is connected to one inlet 23 of a sample tube 11. When oxygen is used to the exclusion of, or in addition to, the inert gas, oxygen is supplied from a source 37 through individual mass flow controllers 39 to the oxygen supply line 29 and the input connection 25 on the inlet 23 of each of the sample tubes.

All or part of the oxygen may be supplied through a relay 31 to a supply line 33, which is connected to an individual supply port 35 between the tubes. In a preferred embodiment, all oxygen is introduced either through the inlets 25 or through the supply ports 35. Oxygen is intermingled with evolved and entrained gases 37, and the oxygen 39 fully oxidizes the entrained pyrolysis or partially oxidized gaseous products 37 in the catalyst 17 within each tube. The oxidized gases flow out through the outlet 41 of each tube 5, and through a conduit 43 to an inlet 45 of a gas cell. The gases then flow out through an outlet 47 to an exhaust 49.

Figure 2:
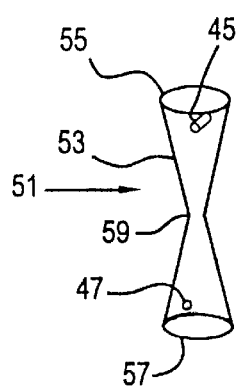
FIG. 2 shows a preferred gas cell.

As shown in FIG. 2, each cell 51 has tapered upper and lower body portions 53, which taper uniformly inward from the cell windows 55 and 57 to a narrow central throat portion 59.

Because the cell is tapered, it reduces volume while still allowing maximum interaction of gas with the light beam within the cell.

As shown in FIG. 1, each cell 51 is mounted on a movable table 61, which is driven by a motor 63 to position each cell sequentially and at timed intervals in alignment with an infrared light beam schematically indicated at 67. A spectrograph receiver schematically shown at 65 receives the light which interacts with the gas within the cell 51 and indicates the gas content and quantities of gas within the cell. The preferred form of a gas detector is a Fourier transform infrared detector (FTIR), of which the electronics and the interferometer are generally indicated in the box 66 attached to the light beam source 67 and the detector 65.

The entire table 61 is enclosed in a heated compartment 69 to maintain the cells at constant temperature.

In a preferred embodiment of the invention, a thermocouple 71 is embedded centrally in the sample 15 to control heat in zone 1 through a processor 73. Heat in the first hot zone 7 is reduced, for example, when thermocouple 71 senses an exothermic reaction within the sample. The processor programs and controls heat in the first and second hot zones 7 and 9, and receives information from the thermocouple 75 which is mounted in each catalyst pack. The processor also controls the mass flow controllers 35 and 39 and relay 31, and receives inputs from pressure transducer 76, which is connected to the gas inlet 25. Processor 73 also receives information from pressure transducer 78 and controls pressure regulation valve 79. The processor also controls the timing and operation of motor 63, which moves the cells into and out of alignment with the FTIR detector.

Figure 3:
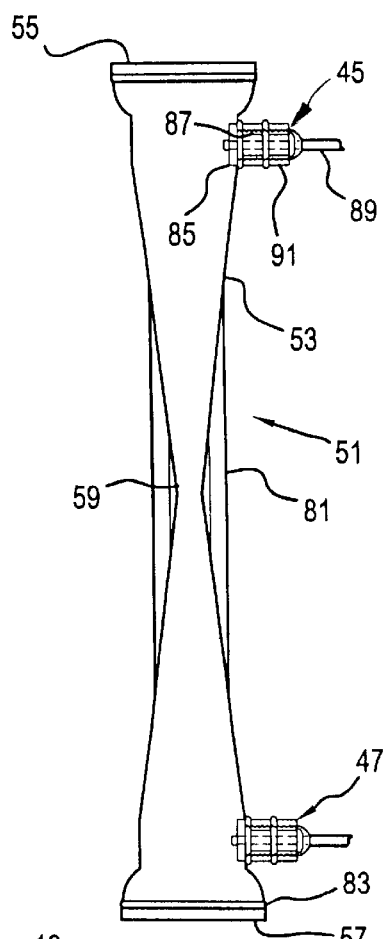
FIG. 3 shows further details of a preferred gas cell.
Figure 4:
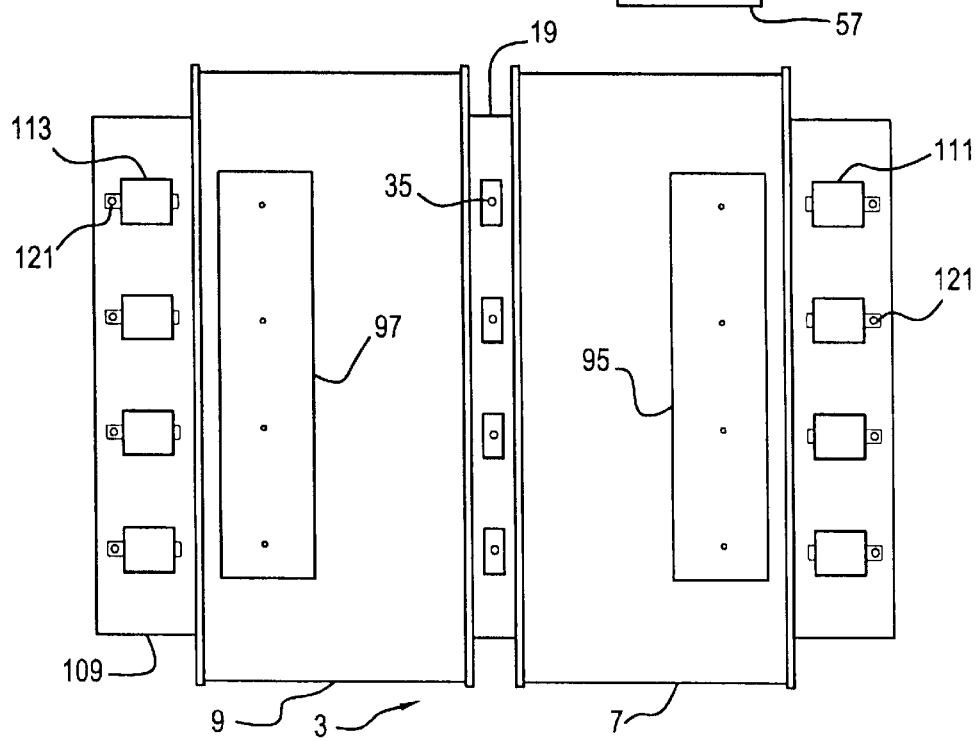
FIG. 4 is a top view of a preferred furnace.

As shown in FIG. 3, the narrow waist 59 of tube 51 is supported by glass rods 81, which are attached to the walls of the upper and lower sections 53.

The calcium fluoride windows 55 and 57 are bonded to the two bodies or are attached by brackets, which are not shown. O-rings 83 seal the cell ends in the enclosure.

Inlets and outlets may be formed as tubes extending from the cells. As shown, inlet 45 and outlet 47 are made of similar structures. A 5/16" or other hole is made in the end of each section 53. A base 85 is bonded in the opening, and a male connector 87 extends outward therefrom. A 1/8" tube 89 is inserted through a 1/8" O-ring, and a cap 91 is threaded onto the connector 87.

In a preferred form of the furnace 3, as shown in FIGS. 47, a base 93 forms a support for the furnace. The furnace is formed with separate sections 7 and 9, which are separately heated by heaters 95 and 97.

The furnace sections have identical construction. Each has a box 101 covered by a cover 103, which is held tight by clamps 105. Handles 107 are used to lift the cover around hinges 109. Lower heaters 99 are identical to the upper heaters. The sections 7 and 9 are separated by bracket 115, which supports a central tube connector 117 with an oxygen fitting 119. Tubes are removable from the furnace sections by opening the covers 103 and pulling the T-handles 121 and releasing the tubes, whereupon tube sections such as sample tube sections 11 may be removed and replaced.

FIG. 6 shows the side elevation of the furnace box 101 with openings 123 for receiving the tubes, and internal small openings 125 which extend through the central mounts 117. The bases 93 are shown as identical brackets connected to the lower furnace boxes by thumb screws 127.

Figure 9:
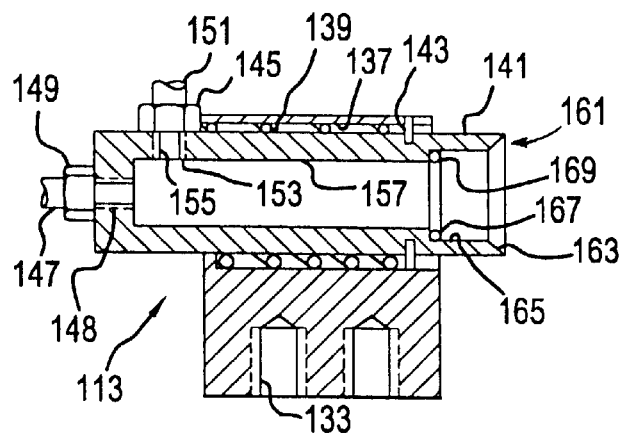
FIG. 9 is a cross-sectional elevation of the end fitting shown in FIG. 8.
Figure 10:
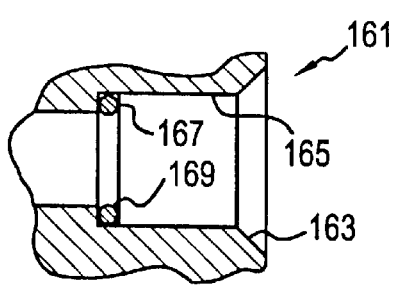
FIG. 10 is a detail of the end fitting shown in FIG. 8.

As shown in the details of FIGS. 8, 9 and 10, the identical end brackets Ill and 113 are formed with rectangular support bodies 131, having drilled and tapped openings 133 for mounting the bases 135 of the blocks 131 on the cantilevered supports 109 shown in FIG. 5.

The blocks have bores 137 which receive springs 139 and sliding barrels 141. A retainer 143 traps spring 139 in the bore 137. A fitting 145 prevents movement of the barrel 141 outward from the bore. The barrel is supplied with a T-handle 121, which is connected to shaft 147. Shaft 147 is connected by threads 148 to an end of the barrel 141. A lock nut 149 threaded on the shaft 147 secures the shaft-barrel connection. Gas tube 151 has a threaded connection 153 with the barrel. An opening 155 in tube 151 communicates with the lumen 157 of the sliding barrel 141.

As shown in FIG. 9 and the detail in FIG. 10, each table 141 has a tube end receiver 161 with a chamfered opening 163 leading to a cylindrical wall 165 to receive a tube end in a slip-fit. A compressible neoprene O-ring 167 rests against radial wall 169 to seal the end of an inserted tube against the wall. To remove or insert a tube, handle 121 is grasped and pulled, pulling shaft 147 and barrel 141 to the left, as shown in FIG. 9, whereupon the tube end 23 or 41 may be slid outward from the cylindrical wall 165.

Figure 11:
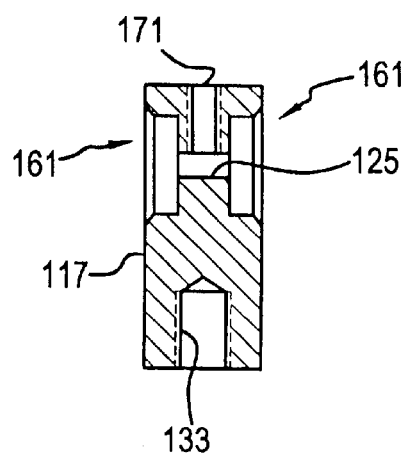
FIG. 11 is a detail of a tube interconnection fitting.
Figure 12:
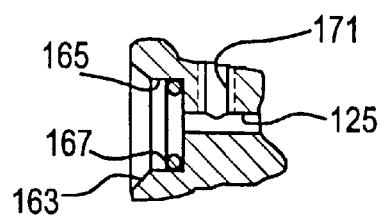
FIG. 12 is a detail of the fitting shown in FIG. 11.

As shown in FIG. 11, the central fitting 117 has opposite tube end receivers 161, which is shown in FIG. 12 to be similar to the receiver 161 shown in FIG. 10. The fitting 117 has two drilled and tapped bolt-receiving openings 133 for attaching the fitting. Oxygen-admitting channel 171 connects with opening 125, which passes between receivers 161 to admit oxygen to the gas flowing through opening 125.

In a preferred embodiment of the invention, the furnace is made of stainless steel sheet material lined with high temperature insulation. The tubes are stainless steel tubes, or more desirably, heat resistant glass, ceramic, or quartz tubes.

The preferred gas cell is made of stainless steel or, more desirably, heat-resistant glass, polymeric materials, quartz or ceramic. A preferred cell is about 18 or 20 cm long and has internal diameters of about 25 mm at the ends and 8 mm at the center.

A metal deposited upon the internal walls of the tapered gas cell body makes these surfaces highly reflective and increases the signal sent to the FTIR detector through an empty gas cell compared to the signal obtained through a gas cell without metal disposition on the internal cell walls.

The effect may be maximized (maximum reflective interaction of the infrared light beam through the gases being analyzed) by positioning a tapered gas cell, which is already aligned in the infrared beam, at a certain point between the entrance and exit windows of the infrared instrument cell compartment, or by slightly misaligning the cell and beam to promote reflection. The effect provides an increase in the interaction of the infrared light beam with a given concentration of gas, and should be of general utility as a gas cell for detecting somewhat lower concentrations of gases compared to a tapered gas cell without metal deposition on the internal cell walls.

Figure 13:
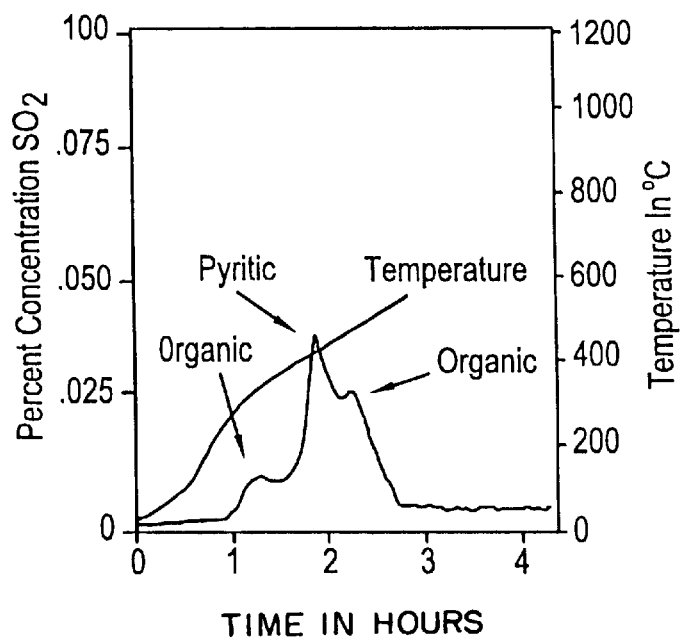
FIG. 13 is a graph of $SO_2$ peaks produced from 10% $O_2$ experiments.

FIG. 13 shows the sulfur dioxide evolution profile resulting from a coal sample thoroughly mixed with tungsten trioxide as diluent and oxidized under the previous TODS conditions of about 100 ml/min. of 10% oxygen in Argon and a linear increase in temperature of 3° C./min. Note that the peak produced from pyrite in the coal appears between the two major peaks produced from the organic sulfur in the coal and is not well resolved from either peak.

Figure 14:
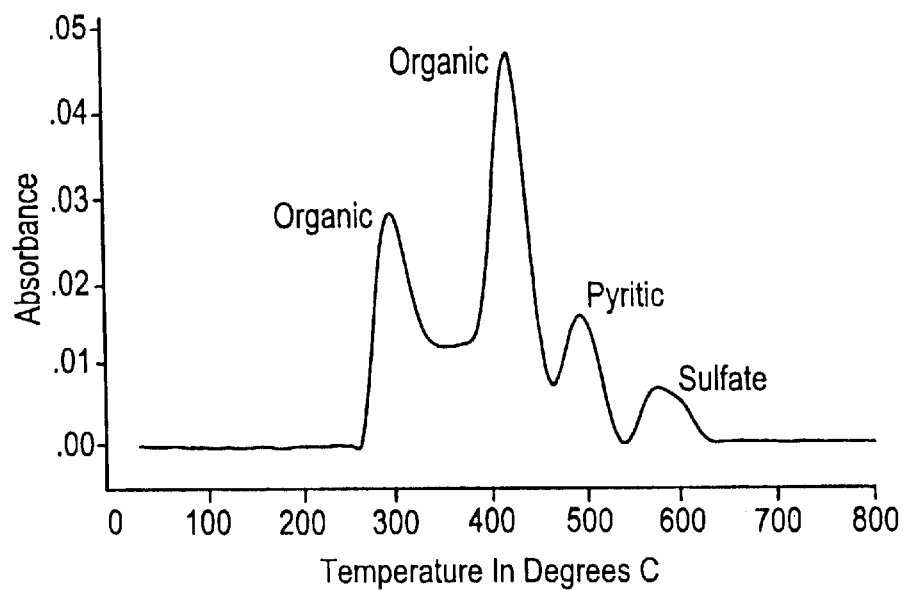
FIG. 14 is a graph of $SO_2$ peaks from 100% $O_2$.

FIG. 14 shows the sulfur dioxide evolution profile resulting from a coal sample thoroughly mixed with celite and oxidized with about 100 ml/min. of 100% oxygen and a linear increase in temperature of 3° C./min. Note that the peak produced from pyrite in the coal appears after the second major peak produced from organic sulfur in coal. Also note that the separation between the pyritic peak and the peak resulting from the second major occurrence of organic sulfur in coal are significantly improved, permitting quantitative estimation of the various types of sulfur in coal.

Table 1 shows sulfur dioxide evolution peaks observed from coal and other substances to a specific structural feature.

EXAMPLE 1

A finely divided, dry, representative sample (50–200 mg with a particle size of –60 Mesh or smaller) is weighed and thoroughly dispersed in approximately 0.6 g of celite and redried for one hour in vacuum at 105° C. The samples are positioned in the combustion tubes between small wads of quartz wool that has been heat treated at 1100° C. for one hour. Any voids in the combustion or catalyst tubes are reduced by positioning quartz rods in the tubes. These rods are also held in place using heat treated quartz wool. The tubes are positioned horizontally in the furnace and control thermocouples are embedded into the sample and catalyst pack. A flow of approximately 100 ml/min. of 100% oxygen is directed through each tube in the first hot zone of the furnace and the FTIR, cell positioner, and data system are set up for data collection. The temperature of the second tube containing the catalyst is quickly raised to at least 1050° C. A linear temperature ramp of 3° C./min. is established in the first hot zone and data collection is initiated. The run is allowed to continue for approximately 5.5 hours until a temperature of at least 1050° C. is obtained. All calculations and graphic hardcopy are completed using the FTIR data system and printer/plotter. Each of the sample tubes in the first hot zone can be used as described above, or any one or more can be used simultaneously to analyze in the pyrolysis mode described below. Any tube in the first and second furnace hot zones can be ramped with a similar or different temperature program. Additionally, the gas flow and pressure control for any of the four sample trains can be the same or dissimilar. The complete operation of the system, including temperature control and monitoring, gas flow, pressure control and monitoring, gas cell positioning unit, and data acquisition, may be under the control of one or more microcomputers.

EXAMPLE 2

Sample preparation, dilution with celite, and insertion into the combustion tube is completed as described above. Alternatively, for pyrolysis studies the undiluted sample can be placed in a small ceramic, quartz, or metal boat and inserted into the combustion tube. The thermocouple is positioned close to the sample as the combustion tube is inserted into the furnace. The second tube containing the catalyst is positioned in the second hot zone and the temperature raised quickly to at least 1050° C. An inert gas flow, normally 50 ml/min. of Argon or helium, is established in the tubes in the first furnace hot zone and normally, a flow of 50 ml/min. of oxygen is established at the inlet of the second tube to continuously oxidize material lost from the sample as the first tube is exposed to a linear temperature increase, normally of 2–10° C./min. The data system and gas cell positioner are powered up and the temperature ramp and data collection are initiated. A run is allowed to continue for approximately 5.5 hours until a temperature of 1050° C. is attained (temperature ramp and final temperature required varies with the sample and may be shorter or longer).

A nonvolatile residue may remain in the first hot zone after the highest pyrolysis temperature desired has been attained. The system may be used in the oxidative mode described above to obtain further characterization of any residue. The furnace may be cooled to room temperature and the same sample tube exposed to an oxygen flow (100 ml/min.) directed into the first furnace hot zone as the temperature is increased in a linear ramp of 210° C./min. or more, depending on the amount and type of residue remaining. The gas cells, cell positioner, and data system are all used as described above to complete the characterization of the residue.

The preferred cell positioning device used to move the cell is of general applicability. Multiple cell applications using cell movement devices are common for ultraviolet-visible spectrometers but have never, as far as is known, been applied to infrared spectrometers, due to interferences and vibration. Multiple cell applications for infrared spectrometers center around use of mirrors to move the light through several stationary cells.

The movement device described above uses a stepping motor driven linear or rail screw positioning table. The preferred embodiment uses a commercially available linear motor to move the cells. The movement is the same. The inventors have adapted the linear motor used to move the cells by adding metal shielding to eliminate electromagnetic interferences to the spectrometer detector and have reduced vibration by mounting the movement device about $\frac{1}{16}$" above the cell compartment so that it does not physically touch the spectrometer. That produces a small, neat package, with the movement mechanism motor and table all being in the cell compartment. The motor for the first linear or rail screw positioning table hangs off the back of the cell compartment. That was somewhat more bulky. However, since the motor was out of the cell compartment it did not have to be shielded. Either or both the linear or rail screw positioning table and the linear motor may be used in a final product.

The cells and cell movement devices work well and may be applied to liquid flow systems as well as to gas flow cell systems. One simply installs conventional or customized liquid flow cells on the table and uses the table and control to operate the system in conjunction with the infrared spectrometer.

This invention provides the new multiple sample furnace, the new cell compartment and the new directed flow, hour glass, gas cell and analytical results based on use of the cell.

The present invention also achieves a better calibration method for water vapor in a gas stream. Normally, one bubbles a gas through water or several different salt/water mixtures if several different concentrations of water vapor are needed. One must set up several bubblers in series to make sure the gas is saturated with water vapor. That method has been used over the years. However, it is time consuming and cumbersome. The present invention uses a gas cylinder containing analyzed mixtures of butane and oxygen in an inert gas such as Argon. Other hydrocarbons such as methane, ethane and propane may be used. The mass flow controlled gas stream is passed through an oven containing an oxidation catalyst, converting the butane quantitatively to carbon dioxide and water. These gases are led directly to the gas cells and serve as a simple, rapid, convenient route to calibrate for both carbon dioxide and water. That allows all of the calibration gases and/or calibration gas precursors to be placed in one cylinder. Water could not have been mixed with sulfur dioxide or nitrogen dioxide in one cylinder, due to reactions between the components in the cylinder. However, hydrocarbons such as butane are compatible with sulphur dioxide and nitrogen dioxide in one cylinder.

One embodiment of the present invention provides multiple sample characterization of coals by controlled-atmosphere programmed-temperature oxidation (CAPTO).

The invention provides the characterization of coals and other high-melting organic solids by use of a new CAPTO apparatus designed for simultaneous analyses of multiple samples. Diluted samples of coals and other high-melting organic solids are subjected simultaneously to an oxidative treatment and a linear increase in temperature and evolve combustion gases intermittently as a function of temperature. For example, distinctive sulfur dioxide evolution patterns are observed among coals of different rank and between raw and treated coals. Plots of concentration vs temperature as well as the total carbon, hydrogen, sulfur, and nitrogen content may be obtained for a number of examples and may be compared to values obtained using ASTM methods.

The new system uses a quad-bore split tube furnace design permitting simultaneous analysis of up to four samples. Each of four first and second hot zones are capable of being heated independently. Temperature ramp, gas flow, and system pressure are all controlled. Software control may be used. A PC-controlled FTIR equipped with multiple gas cells and cell positioner is used as the detector for the system. The instrument is designed for use in an oxidative mode, pyrolysis mode, or any inert gas/oxygen combination.

The gas generating and furnace side may be controlled by a computer system design for a controlled-atmosphere programmed-temperature oxidation (CAPTO) apparatus used in coal characterization.

Current PC software and the hardware interfaces are available for control of a CAPTO apparatus capable of simultaneous analysis of multiple coal samples.

The apparatus includes furnaces with eight independently controlled hot zones. Temperature ramp, gas valves, gas pressure and flow may all be under software control.

The detector is a PC-controlled FTIR spectrometer equipped with multiple gas cells on a stepper-motor positioning table. The apparatus utilizes one direct memory access (DMA) channel, 10 PID control loops, one serial channel, 48 analog and 21 digital input/output lines. A first phase involved installation of a 486 PC-controlled FTIR. Custom application software runs within LabCalc (Galactic Industries, Salem, NH), and controls acquisition of spectra over time and temperature. Upon installation of new furnaces and related sensors and controllers, a second 486 PC was used, running custom application software within VIEWDAC (Keithley Asyst, Rochester, N.Y.). A final phase controls the entire apparatus from a single PC.

The invention provides a multiple-cell design for the rapid analysis of several gas steams by fourier-transform infrared spectrometry.

The gas flow cell configuration achieves rapid, simultaneous analysis of multiple gas streams produced from controlled-atmosphere programmed-temperature oxidation (CAPTO). Resolution and quantitative analysis with CAPTO as detected by evolved gases is enhanced by relatively slow rates of temperature increase. Sample throughput for CAPTO can be improved by oxidizing several separate samples simultaneously and monitoring each experiment individually.

A multiple furnace configuration incorporates multiple gas flow cells and a linear positioning device to carry out sequential interrogation of several separate gas streams using a single FTIR spectrometer. The individual gas cells have reduced volume compared to conventional cells of the same overall length and width. Cell clearing time is improved by a combination of beam-conforming envelope and directed gas inlet flow. The use of front surface metal coatings provides for increasing radiant power. The mounted gas cells are positioned in the FTIR sample compartment by a single x or y axis or turret positioning device under computer control. Cell mountings and operational approaches were developed to maintain long-term positional stability (repeatability) and sensitivity. All parameters were compared to a single cell system and results indicate the performance (along with the compact size, and ease of implementation) make the invention preferable to other multiplexing approaches. The invention is widely applicable.

Figure 15:
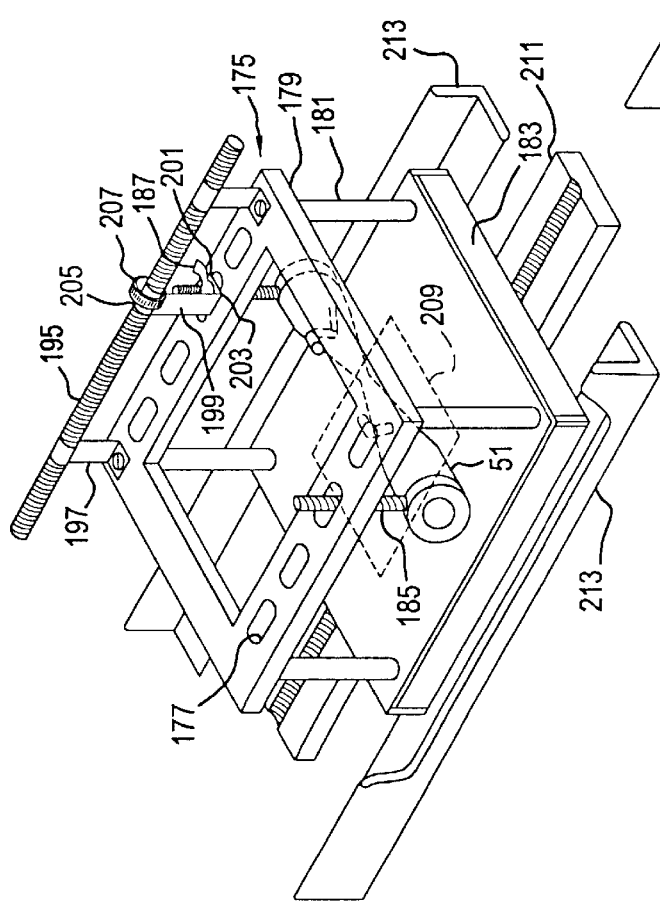
FIG. 15 is a schematic perspective view of a cell positioning table and alignment mechanism.

FIG. 15 shows a cell 51 suspended from an adjustment frame 175 with openings 177 for holding several cells. The frame has a rectangular top 179 supported on legs 181 above table 183.

Figure 16:
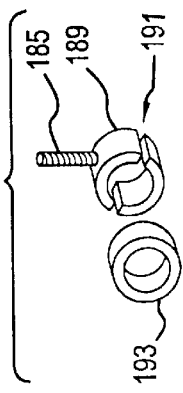
FIG. 16 is a detail of a cell end mounting.

As shown in detail in FIG. 15 and 16, y axis adjustment is provided by threaded rods 185 and wing nuts 187. Rods 185 are welded to upper halves 189 of externally threaded split rings 191. Ends of cells 51 are inserted in the split rings and threaded nuts 193 clamp the rings on the cell ends. Turning wing nuts 187 control y axis adjustment to align the cells between an infrared source and a detector.

Parallel threaded rods 195 are held above the frame top 179 on supports 197. Slides 199 with devises 201 at the bottoms 203 and top 205 provide adjustment in the x axis. Thumb wheels 207 in the top devises move the slides and the rods 185 along the openings 177 to adjust the cells in the x direction.

A linear motor 209 beneath the table 183 cooperates with fixed motor platen 211 to smoothly slide the table to sequentially align the cells with the infrared source and detector. Shields 213 along the sides of the table prevent stray electromagnetic radiation and magnetic fields from reaching the detector.

Table 183 may be replaced by a barrel-shaped turret with cells 51 cylindrically aligned for sequential positioning between the source and detector.

Figure 17:
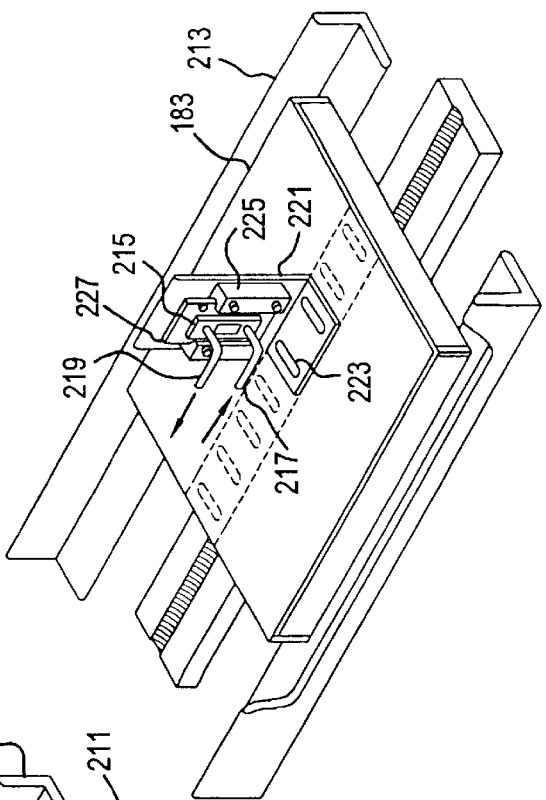
FIG. 17 is a perspective schematic representation of a liquid cell on a movable tube.

FIG. 17 shows one of a number of liquid cells 215 with a liquid inlet 217 and an outlet 219 mounted on the table in place of the gas cells. A cell holder 221 is fixed to the table with adjustable connectors on base 223. Blocks 225 mounted on a centrally slotted vertical portion of holder 22 adjustably receive a centrally open cell mount 227 on which the cell is fixed. The linear motor moves the liquid cells to sequentially align the cells and the thin liquid films therein with the IR source and the detector.

The cells are made of thin IR transparent materials. Shielding 213 isolates electromagnetic fields from the detector.

Figure 18:
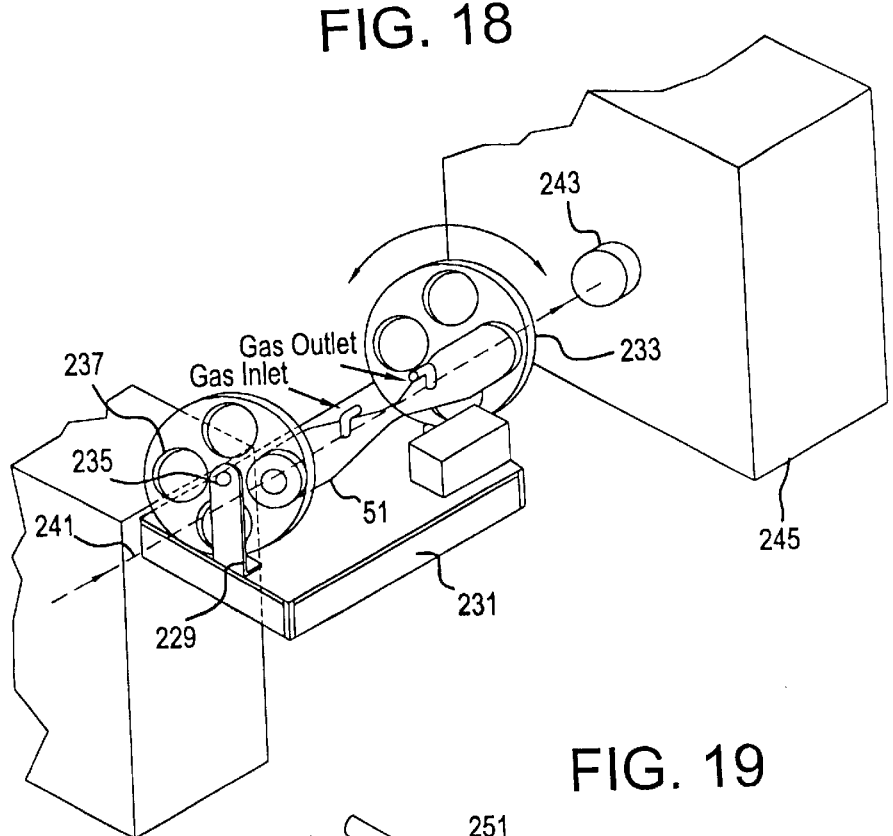
FIG. 18 is a perspective schematic representation of a turret cell positioning device.

FIG. 18 shows a preferred turret. Bearing blocks 229 are mounted at ends of a fixed table 231. Rotary holders 233 are mounted on axles 235. Ends of cells 51 are mounted in openings 237. A stepper motor 239 drives one or both rotary holders 233 to sequentially align a cell 51 with an infrared light beam 241 and a detector 243. The apparatus is enclosed within a cell compartment 245.

Figure 19:
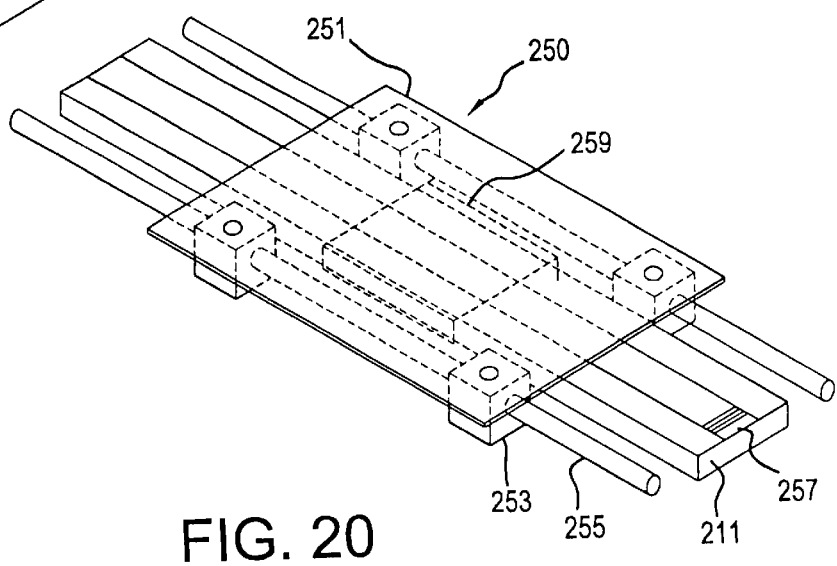
FIG. 19 is a perspective schematic view of a multiple cell mounting plate with linear bearings for moving along support rods by a linear motor and platen.

A preferred mounting or multiple cells is generally indicated by the numeral 250 in FIG. 19. Mounting plate 251 is secured to four linear bearings 253 with recirculating balls mounted in tracks. The recirculating balls contact and move along rods 255 with substantially frictionless motion. The recirculating balls in the linear bearings 253 support the mounting plate 251 on the support rods 255. Ends of the support rods are mounted in the housing, which is not shown.

The fixed platen 211 is mounted on the machine housing and has a series of grooves 257 which magnetically engage with complementary movable structure on the forcer 259, which is connected to the mounting plate. The forcer moves along the platten.

As previously described, the forcer motor moves the cells which are mounted on the mounting plate 251 in stepped sequences along the platen 211. The support rods 255 and the linear bearings 253 supply smooth uniform motion.

Figure 20:
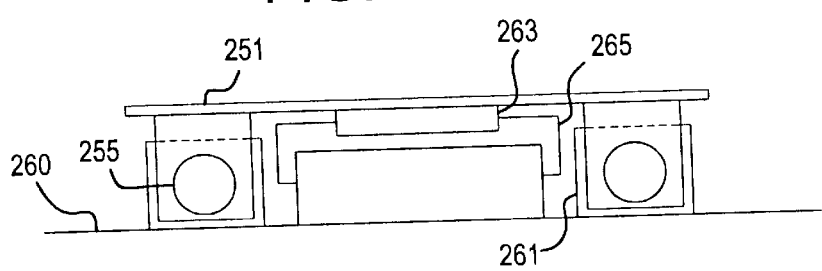
FIG. 20 is an end elevation schematic view of the multiple cell mount shown in FIG. 19.

An end view of the system is shown in FIG. 20. The housing base is generally indicated by the numeral 260. Mounts 261 are connected at spaced locations on the housing 260 to support the support rods 255. The linear bearings 253 move along the support rod and are connected to the moving mounting plate 251. In a preferred embodiment, retaining brackets 263 are mounted beneath the mounting plate and are close against the forcer motor housing 265 to provide precise movement along the fixed platen 211.

Figure 21:
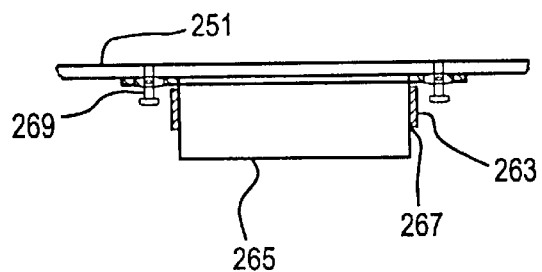
FIG. 21 is a schematic side detail of the mount shown in FIGS. 19 and 20.

Brackets 263 are shown in FIG. 21. The brackets are connected by the bolt attachment 267 or other attachments to the forcer motor. Bolts 269 extend through slots in the mounting plate to provide adjustment of the angle iron brackets 263. The bolts are tightened so that force is precisely transferred from the forcer to the mounting plate for providing correct alignments.

Figure 22:
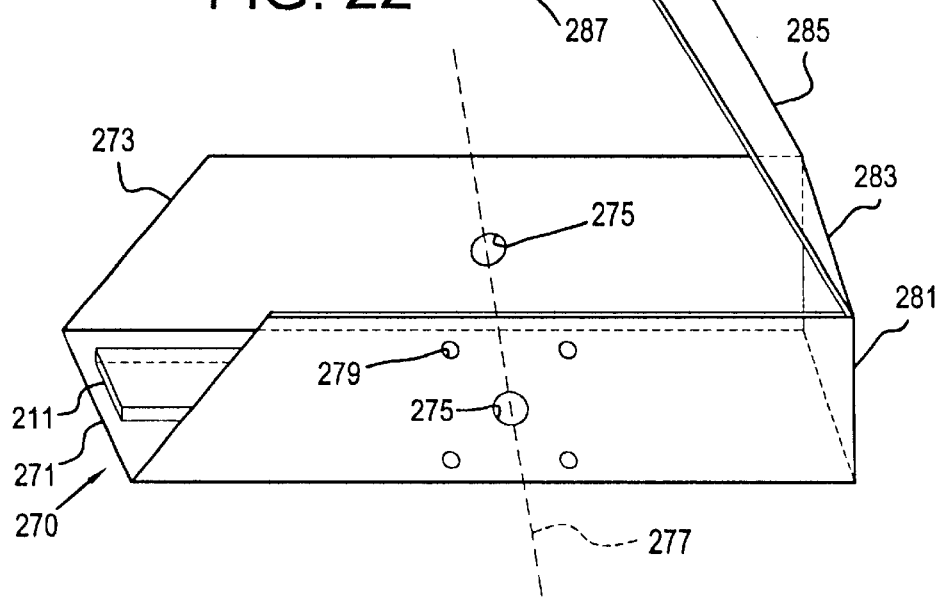
FIG. 22 is a schematic perspective view of a cell positioner housing.

As shown in FIG. 22, platen 211 is connected to the instrument base through an intermediate housing 270. The housing has a bottom 271 and two vertical side walls 273 with openings 275 for the FTIR beam 277. Mounting holes 279 are provided in the base 271 for aligning, connecting and fixing the steel housing 270 to the FTIR instrument. An end wall 281 has an upper hinge 283 to which a top wall 285 is connected. A sloping end wall 287 is connected to the top wall. Flexible gas connections to the cells extend through slots in the base or through slots in the side walls 273 or end walls 281 or 287.

The lid 285 as shown in FIG. 22 is preferably non metal, while the side walls 273, end wall 281 and base 271 are metal.

Figure 23:
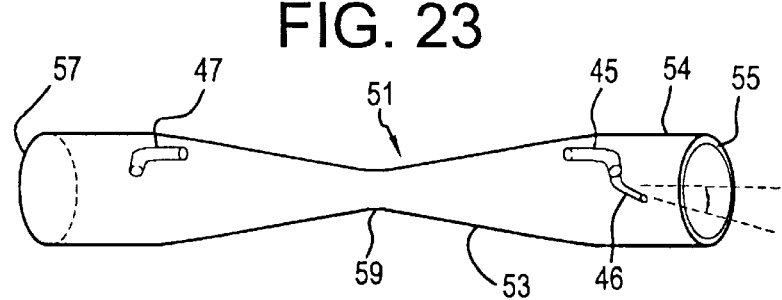
FIG. 23 is a schematic representation of a preferred gas analysis cell.

As shown in FIG. 23, the preferred embodiment of the gas analysis cell 51 has a narrow waist portion 59, an inlet 45 and an outlet 47. The inlet has an internal fixed tube 46 to admit gas at an angle to the side wall and end 55 for promoting full and rapid purging and replacement of gas in the cell. The preferred embodiment of the cell 51 has flat end faces 55 which are windows for the infrared ray, and the sloping wall portions 53 terminate in cylindrical portions 54, which extend between the sloping portions and the end faces.

The positioning table may be used with liquid cells for analytical testing of liquids. In that case, thin film liquid cells are plates along which thin films of liquid flow or which are coated by the liquid to be tested. The plates are suspended from a frame mounted above a table. The plates are moved in x and y axis for alignment by threaded rods, thumb wheels and wing nuts. Once aligned, the plate-like cells are moved sequentially into alignment with the source and detector by a linear motor mounted in the table.

The preferred method of calibrating for carbon dioxide and water includes oxidizing fuel gas in a mass flow controlled relationship and flowing the resultant carbon dioxide, water vapor and inert gas to the device being calibrated. One preferred method uses an analyzed mixture of oxygen, an inert gas and a substance containing carbon and hydrogen with or without other elements and oxidizes the substance, using the resultant gases and water vapor as calibration standards.

For example an analyzed mixture of a fuel gas such as butane, oxygen, sulphur dioxide and nitrogen dioxide and an inert gas such as argon can be used from one cylinder to provide a standard calibration mixture for carbon dioxide, water vapor, sulphur dioxide and nitrogen dioxide. Another example uses methylamine, oxygen and an inert gas such as argon as the source of calibration gases of carbon dioxide, water vapor, nitrogen dioxide and argon.

While the invention has been described with reference to specific embodiments, modifications and variations of the invention may be constructed without departing from the scope of the invention, which is defined in the following claims.

I claim:

1. A gas analysis cell comprising a solid body having a first generally cylindrical end portion, a first sloping conical portion extending from the first cylindrical end portion to a throat narrower than the first end portion, a second sloping conical portion extending outward from the throat, a second cylindrical end portion connected to a diverging end of the second sloping conical portion, and first and second opposite end faces for transmitting energy, an inlet connected to the first cylindrical portion proximal the first end face, and having an outlet connected to the second cylindrical portion for introducing, purging and replacing gas to be analyzed into and out of the cell, further comprising an inlet director connected to the inlet for directing gas toward the first end face at an angle to the cylindrical end portion and at an acute angle to the first end face.

2. The gas analysis cell of claim 1, wherein the body is transparent.

3. The gas analysis cell of claim 1, wherein the first and second sloping conical positions are similar in shape.

4. The gas analysis cell of claim 1, wherein the body has a uniform wall thickness.

5. The gas analysis cell of claim 1, wherein the end faces are cell windows.

6. The gas analysis cell of claim 1, wherein the end faces are cell windows, and further comprising a focused spectrometer beam source aligned with one window and a spectrometer detector aligned with the other window.

7. The gas analysis cell of claim 1, wherein the cell body is glass.

8. The gas analysis cell of claim 1, further comprising an inlet tube connected within one end of the cell body.

9. The gas analysis cell of claim 1, further comprising suspenders connected to the cylindrical end portions of the cell for suspending the cell.

10. The gas analysis cell of claim 1, wherein the end faces are cell windows, further comprising a focused spectrometer beam source aligned with one window and a spectrometer detector aligned with the other window, and further comprising shielding adjacent the cell for preventing stray electromagnetic radiation and magnetic fields from reaching the cell or detector.

11. A plurality of gas analysis cells, each cell comprising a solid body having a first generally cylindrical end portion, a first sloping conical portion extending from the first cylindrical end portion to a throat narrower than the first end portion, a second sloping conical portion extending outward from the throat, a second cylindrical end portion connected to a diverging end of the second sloping conical portion, and first and second opposite end faces for transmitting energy, an inlet connected to the first cylindrical portion proximal the first end face, and having an outlet connected to the second cylindrical portion for introducing, purging and replacing gas to be analyzed into and out of the cell, further comprising the plurality of the gas analysis cells being arranged in parallel axial relationship on a mounting plate, plural parallel bearings connected to the mounting plate, and plural parallel rails connected to the bearings transverse to the parallel axes of the gas cells, rail mounts for mounting the rails on a fixed bed, and a plate driver connected between the mounting plate and the fixed bed for sequentially driving the mounting plate and the bearings along the rails for sequential alignment of the axes of the analysis cells with an energy source and an energy detector for transmitting energy into and out of the cells and analyzing gaseous content of the cells.

12. The apparatus of claim 11, wherein the motion producer comprises a platen connected to the fixed base beneath the plate and parallel to the rails, and a forcer mounted beneath the plate above the platen for moving the plate along the platen and rails.

13. The apparatus of claim 11, further comprising a housing connected to the base and surrounding the rails, platen, plate and cells, the housing having a base portion and first and second opposite parallel side wall portions, a first end wall connected to ends of the side wall and to the base portion, a hinge connected to an upper edge of the first end wall, a lid connected to the hinge and a second end wall connected to an end of the lid opposite the hinge, the side wall portions having energy transparent openings for alignment with the energy source and the energy detector.

14. A gas analysis cell comprising a solid body having a first generally cylindrical end portion, a first sloping conical portion extending from the first cylindrical end portion to a throat narrower than the first end portion, a second sloping conical portion extending outward from the throat, a second cylindrical end portion connected to a diverging end of the second sloping conical portion, and first and second opposite end faces for transmitting energy, an inlet connected to the first cylindrical portion proximal the first end face, and having an outlet connected to the second cylindrical portion for introducing, purging and replacing gas to be analyzed into and out of the cell, further comprising an inlet tube connected within one end of the cell body, wherein the inlet tube extends into the body and has an opening directed angularly toward an end face of the body for rapid purging and filling of the cell.

15. A gas analysis cell comprising a solid body having a first generally cylindrical end portion, a first sloping conical portion extending from the first cylindrical end portion to a throat narrower than the first end portion, a second sloping conical portion extending outward from the throat, a second cylindrical end portion connected to a diverging end of the second sloping conical portion, and first and second opposite end faces for transmitting energy, an inlet connected to the first cylindrical portion proximal the first end face, and having an outlet connected to the second cylindrical portion for introducing, purging and replacing gas to be analyzed into and out of the cell, further comprising suspenders connected to the cylindrical end portions of the cell for suspending the cell, wherein the suspenders are adjustable.

16. A gas analysis cell comprising an axially elongated cell body in a shape of a body of revolution formed about an elongated axis, the body having a uniform thickness non-porous wall, a central waist portion, first and second tapered portions extending axially in opposite directions from the waist portion and uniformly tapering radially and axially outwardly from the waist portion, the waist portion being narrower than the first and second portions, end portions on outer ends of the tapered portions and radially extending windows at outer axial ends of the end portions closing the cell body, an inlet near one end of the cell body and an outlet near another end of the cell body, further comprising an internal tube fixed to the inlet and extending into the cell body, wherein the internal tube is fixed at an angle to the wall for admitting gas at an angle to the wall and at an angle to one of the radially extending windows for promoting full and rapid purging and replacement of gas in the cell.

17. A gas analysis cell comprising a body having a first portion extending to a throat narrower than the first end portion, a second portion extending outward from the throat, and first and second opposite end faces for transmitting energy, an inlet connected to the first portion proximal the first end face, and an outlet connected to the second portion for introducing, purging and replacing gas to be analyzed into and out of the cell, further comprising an inlet director connected to the inlet for directing gas toward the first end face at an angle to the first portion and at an acute angle to the first end face.

18. The gas analysis cell of claim 17, further comprising adjustable suspenders connected to the cell for adjustably suspending the cell.

* * * * *